United States Patent [19]

Henderson et al.

[11] Patent Number: 5,101,968
[45] Date of Patent: Apr. 7, 1992

[54] RETAINERS FOR NEEDLED SURGICAL SUTURES

[75] Inventors: Scott Henderson, Albuquerque; James A. Wimbush, Rio Rancho, both of N. Mex.

[73] Assignee: Lukens Medical Corporation, Rio Rancho, N. Mex.

[21] Appl. No.: 696,611

[22] Filed: May 7, 1991

[51] Int. Cl.$^5$ .............................................. A61B 17/06
[52] U.S. Cl. ..................... 206/63.3; 206/227
[58] Field of Search ............... 206/63.3, 438, 491, 206/492, 380, 227

[56] References Cited

U.S. PATENT DOCUMENTS

| | | | |
|---|---|---|---|
| 4,120,395 | 10/1978 | Mandel et al. | 206/63.3 |
| 4,896,767 | 1/1990 | Pinheiro | 206/63.3 |
| 4,946,043 | 8/1990 | Roshdy et al. | 206/63.3 |
| 5,024,322 | 6/1991 | Holzwarth | 206/63.3 |

Primary Examiner—Paul T. Sewell
Assistant Examiner—Jacob K. Ackon, Jr.
Attorney, Agent, or Firm—John D. Kaufmann

[57] ABSTRACT

A suture retainer includes a first panel and foldably connected second through fifth panels. When all of the panels are folded, the retainer has the approximate size and shape of the first panel, and the suture is contained within the folded panels. Separator facilities on the first panel prevent suture strands from becoming tangled. The separator may constitute a pleated low friction sheet with the strands contained between the plats, or it may constitute one or more sinuous cuts in the first panel which define tabs for holding the strands. Sutures are withdrawn from a site at one end of the first panel. The second panel is foldably located at the other end of the first panel and maintains suture strands within the boundary of the first panel. The third panel is foldable about a side of the first panel to overly the folded second panel, the separator and the sutures and to complimentarily overly the first panel. A holder, such as a foam strip on the first panel and near the withdrawal site, holds the suture strand to maintain the needle strand attachment point at the withdrawal site. Facilities normally cover the needlepoints at the withdrawal site. These facilities may constitute either a tab on the third panel, which covers the needlepoints when the third panel is folded, or a removable sheath on the needles. Tabs on the third panel fit into slits at the boundary of the first and fourth panels to keep the third panel folded.

46 Claims, 6 Drawing Sheets

RETAINERS FOR NEEDLED SURGICAL SUTURES

BACKGROUND OF THE INVENTION

The present invention relates to retainers for needled surgical sutures, and, more particularly, to such retainers which are economical to manufacture and easy to use and which perform their retention and protective functions in an expedient manner.

Typical suture retainers are packages which comprise folded paper structures for retaining one or more sutures. As used herein, "suture" refers to a suture strand, one or both free ends of which are attached to respective surgical needles. The retainer may be contained in one or more sterile, hermetic envelopes. To use the suture, the envelopes are removed and the retainer is partially or wholly opened or otherwise manipulated to provide access to the needles. Each needle may be grasped with a forceps and pulled from the retainer resulting in withdrawal of the trailing suture strand.

Suture retainers are intended to protect sutures from mechanical and microbial degradation during shipping, handling and storage, while allowing the sutures to be removed with a minimum of difficulty. Prior art suture retainers of this general type include those described in the following U.S. Pat. Nos. 4,615,043; 4,896,767; 4,887,710; 4,884,681; 4,708,241; 4,615,435; 4,574,948; 4,574,957; 4,572,363; 4,555,016; 4,496,045; 4,491,218; 4,483,437; 4,427,109; 4,413,727; 4,412,614; 4,412,613; 4,416,363; 4,253,563; 4,284,194; 4,249,656; 4,120,395; 4,089,409; 4,063,638; 3,939,969; and D22,600.

A primary object hereof is the provision of suture retainers which exhibit to a maximum extent the desirable characteristics thereof.

SUMMARY OF THE INVENTION

With the above and other objects in view, the present invention contemplates a retainer for a suture having a suture strand and a needle attached to one or to each free end of the strand. The retainer includes a first panel with second through fifth panels foldably connected thereto. When all of the panels are folded, the retainer has the approximate size and shape of the first panel. The suture is contained within the folded panels.

A separator on the first panel prevents tangling of the suture strand during withdrawal, facilitates such withdrawal, and, where multiple sutures are retained, keeps their respective strands separate. The separator may be one or more two-leaved, low friction and robust envelopes or an accordion-folded sheet of a low friction, robust material. Alternatively, the separator may be one or more sinuous cuts in the first panel which define adjacent tabs and beneath which the strand may be frictionally held.

A suture-withdrawal site resides at one end of the first panel. The second panel, at the other end of the first panel, is foldable to prevent the strand from residing beyond the boundary of the first panel and when so folded may overlie a part of the separator. The third panel is foldable about a side of the first panel to overlie the folded second panel, the separator and the suture and to complementarily overlie the first panel, while not overlying the withdrawal site. A holder, which may be a foam strip with or without slits and mounted to the first panel, frictionally (where it has slits) or mechanically (where it does not have slits) holds the suture strand to maintain the needle and the needle-strand attachment at the withdrawal site.

Facilities may cover the needle point at the withdrawal site. These facilities may be a tab on the third panel, which covers the needle points when the third panel is folded, or a sheath removably mounted to the needles. In either event, these covering facilities are separate from and independent of the fifth panel.

Tabs on the third panel which fit into slits at the boundary of the first and fourth panels may be used to keep the third panel folded.

When the fourth panel is folded about the other side of the first panel, it partially or completely overlies the folded third panel. The fourth panel may be maintained folded by a locking tab defined in its free edge by a transverse slit. The locking tab fits under a locking ear formed in the first and third panels. The locking ear is produced by a V-shaped cut formed in the first and third panels. When the third panel is folded, the legs of the V are superjacent and the wedge-like locking ear is formed.

The fifth panel may constitute either (a) a separable cover portion of or a separate member from the fourth panel, which is in either case mutually foldable with the fourth panel and unfoldable independently therefrom, or (b) a separate panel foldable about the one end of the first panel. Unfolding the fifth panel exposes the withdrawal site to permit suture removal. The fifth panel may be maintained folded in the same way as the fourth panel or by a tab thereon fitting into a slot in the third panel. In cases where the folded fourth panel only partially covers the second panel, an adhesive, indicia-bearing label may be affixed to the third and fourth panels to secure the retainer by ensuring its folded condition and to identify its contents.

DETAILED DESCRIPTION

Figure 1:
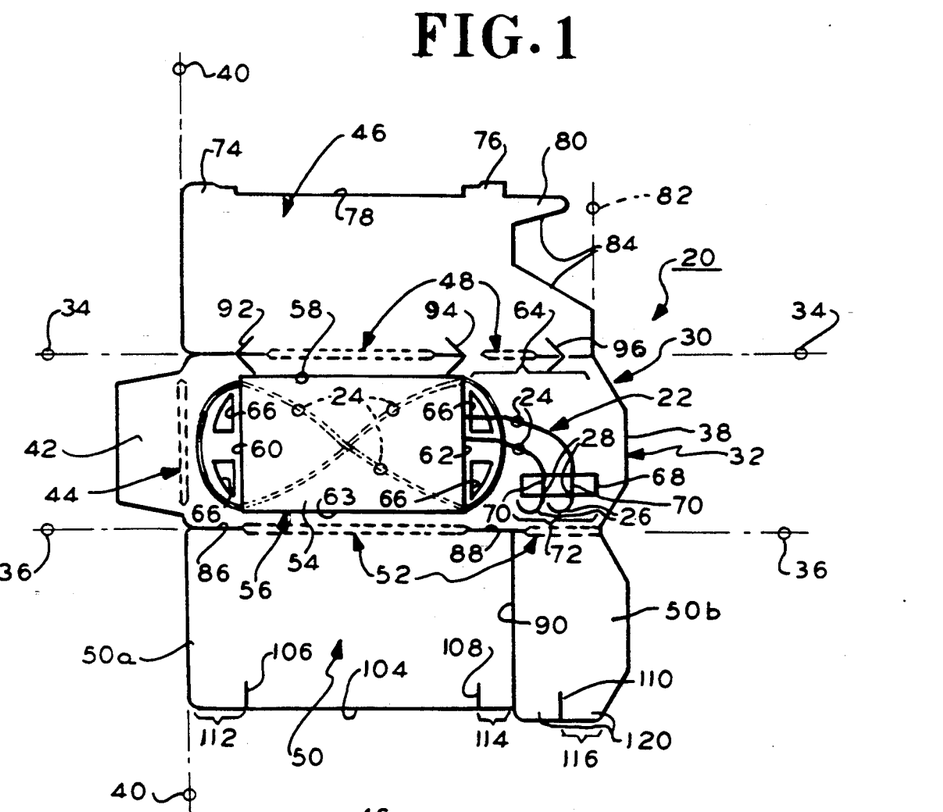
FIG. 1 is a plan view of a first embodiment of a suture retainer according to the present invention, the retainer being unfolded.

Referring first to FIG. 1, there is shown a first embodiment 20 of a suture retainer for retaining one or more sutures 22, each of which comprises a suture strand 24 and one or more surgical needles 26. The needles 26 are attached to free ends 28 of the suture strand 24 in any convenient fashion. In FIGS. 1-4, the suture 22 comprises a single suture strand 24 with a needle 26 attached to each free end 28 thereof. The retainer 20 of could also, of course, be used with a plurality of sutures 22 each comprising a suture strand 24 and a single needle 26 attached to one free end 28.

The retainer 20 is stamped or die cut as a generally irregular planar member 30 from an appropriate robust paper or card such as medical grade S.B.S. bleached white or other suitable material.

The planar member 30 is initially flat and includes a first generally rectangular panel 32 defined by opposed, parallel longitudinal boundaries, edges or fold lines 34 and 36 and opposed, parallel transverse boundaries, edges or fold lines 38 and 40 which are normal to the edges 34 and 36. A second generally rectangular panel or flap 42 is integral with the panel 32 along the boundary or fold line 40. The second panel 42 is foldable relative to the first panel 32 via a folding gusset 44 or a similar facility such as score lines, double perforated fold lines, or the like, present along the boundary 40.

A third generally rectangular panel 46 is integral with the panel 32 along the boundary 34. The third panel 46 is foldable relative to the first panel 32 via one or more folding gussets 48 or similar facilities present along the boundary 34. A generally rectangular panel 50 is also integral with the panel 32 along the boundary 36 and is similarly foldable via one or more folding gussets 52 or the like present along the boundary 36. The panels 46 and 50 are generally rectangularly complementary to the panel 32 except as noted hereinafter. The second panel 42 is substantially shorter along its shorter dimension than the long dimension of the panel 32.

The suture strand 24 is preferably wound in a figure-8 pattern and is held between the low-friction leaves 54 of a separator 56, only a top leaf 54 of which is visible in FIG. 1. As viewed in FIG. 1, the separator 56 has two leaves 54 folded along a hinge line 58. The separator may comprise a sheet of suitable robust, low-friction material, such as sterilizable (e.g., ETO and/or Gama) blue or natural glassine, folded along the hinge line 58 to form a rectangular separator 56 which is somewhat smaller than the first panel 32. The separator 56 may be mounted to the first panel 32 by the use of a suitable adhesive, such as an FDA-approved cyano-acrylate-ester adhesive. The separator 56 is mounted to the surface of the panel 32 so that its left lateral edge 60 is closer to the boundary 40 than the spacing of its right lateral edge 62 from the boundary 38. The fold line 58 and the opposed longitudinal edges 63 of the leaves 54 are substantially respectively equidistantly spaced from the boundaries 34 and 36. The foregoing relative positioning of the panel 32 and the separator 56 creates an open region 64 on the surface of the panel 32 for purposes described below.

To aid in winding the suture strand 24, the first panel includes a plurality of apertures 66 through which winding posts (not shown) may selectively protrude. With the posts protruding through the apertures 66, the strand 24 is wound thereabout in a figure-8 while the upper leaf 54 of the separator 56 is held open along the hinge line 58 to lie against the third panel 46. After the strand 24 has been wound in the figure-8 or other selected pattern, the posts are withdrawn and the upper leaf 54 is folded thereover. See U.S. Pat. Nos. 4,574,957; 4,574,948; 4,412,614; and 4,069,912 for a variant of this winding technique (not involving, however, a separator 56). The low-friction nature of the separator 56 facilitates easy tangle-free withdrawal of the strand 24 and, hence, easy release of the suture 22 in use. Where multiple sutures 22 and multiple suture strands 24 are held in the retainer 20, the separator 56 may comprise an accordion-folded sheet with one figure-8 wound strand 24 of each suture 22 between adjacent leaves 54. In this event, the separator 56 prevents the suture strands 24 from becoming entangled with each other. In all cases, the separator 56 prevents the strand 24 from taking an undesirable set, a problem which is acute with strand 24 such as monofilament polypropylene.

A strip 68 is mounted within the open region 64 to the first panel 32 by a suitable adhesive (not shown), such as an FDA-approved pressure-sensitive adhesive. The strip 68 is preferably a medical grade plastic foam onto which the adhesive is previously coated. The strip 68 is located between the boundary 38 and the edge 62 and is proximate to and parallel with the boundary 36. Formed in the strip are parallel, spaced suture-holding slits 70. Before the strand 24 is wound, its free ends 28 with the attached needles 26 are located so that the walls of the slits 70 frictionally engage either a portion of the needle 26 and the strand 24 or the strands 24 only up to the attachment of the needles 26 to the free ends 28. To this end, the density or grade of the strip 68 may be varied to vary the frictional engagement force. This engagement holds the needles 26 stationary during winding of the strand 24 and maintains the needles 26 spaced apart and stabilized at a suture-withdrawal site 72 within the region 64. The withdrawal site 72 is located quite near to the boundary 36 of the first panel 32 and between the edge 62 and the boundary 38.

After the suture 22 is held by the strip 68 and the strand 24 is wound, the second panel 42 is folded along the boundary 40 to overlie the edge 60 of the separator 56 and any of the loop-like portion of the figure-8 wound strand 24 which may protrude past such edge 60. The folded panel 42 insures that the wound strand 24 is retained within the perimeter of the first panel 32 and does not extend beyond the boundary 40 where it could snag or be damaged.

The third panel 46 includes closing tabs 74 and 76 formed on the free longitudinal boundary or edge 78 thereof. The third panel also includes a needle-covering tab 80. The tab 80 may be conveniently produced by removal of some of the material of the panel 46 along a transverse boundary or edge (shown in phantom at 82)

to produce an opening 84 adjacent the tab 80. The tab 80 and the opening 84 are dimensioned and located so that when the third panel 46 is folded along the boundary 34 to overlie the second panel 42 and the separator 56 (FIG. 2) the tab 80 covers the points of the needles 26, while the shanks of the needles 26 and the free ends 28 of the strands 24 at the withdrawal site 72 are exposed through the opening 84. In this manner, the points of the needles 26 are covered and protected by the tab 80 while permitting the sutures 22 to be selectively withdrawn. Withdrawal of the sutures 22 is achievable by grasping a selected needle 26 with forceps near the free end 28 of its strand 24, lifting the needle 26 slightly to free the strand 24 from its slit 70 and moving the now freed suture 22 rightwardly (in FIGS. 2 or 4) until the needle 26 clears the tab 80. The suture 22 is then withdrawn by pulling the strand 24 out of the separator 56 while uncoiling the figure-8. If the needles 26 are attached to opposite free ends 28 of a single strand 24, continued unwinding of the figure-8 will ultimately withdraw the other needle 26 from its slit 70 and out from beneath the tab 80.

The boundary 36 contains slits 86 and 88 into which the tabs 74 and 76 may be respectively inserted after the third panel 46 has been folded to overlie the first panel 32. See FIG. 2. This locks and maintains the folded panel 46 in its folded position.

The panel 50 comprises a main portion 50a and a cover portion 50b. The portions 50a and 50b may be integral but be easily separable along a score line or partial cut 90. Alternatively, numeral 90 may designate a boundary between portions 50a and 50b which are not integral therealong but are commonly foldable about the boundary 36. In either event, the main portion 50a by itself may be viewed as the fourth panel, while the cover portion 50b may be viewed as a fifth panel.

Figure 2:
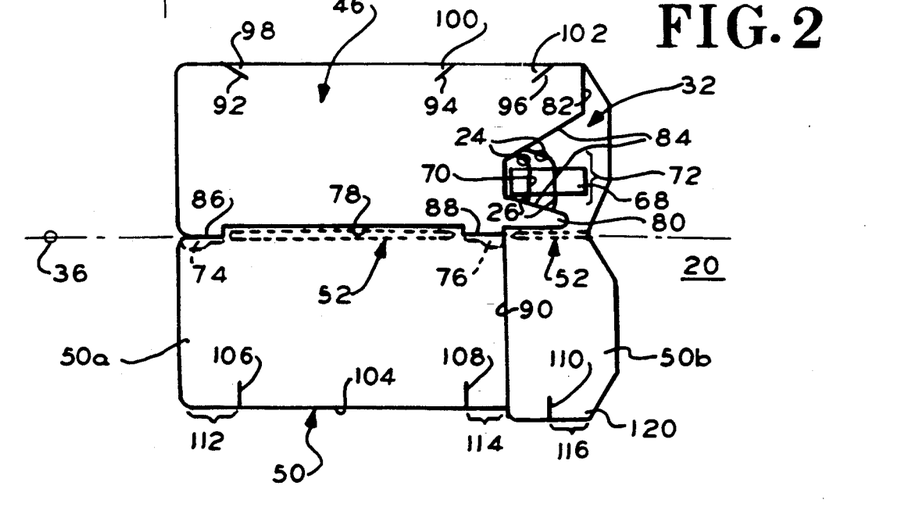
FIG. 2 is a plan view of the retainer of FIG. 1 partially folded.
Figure 3:
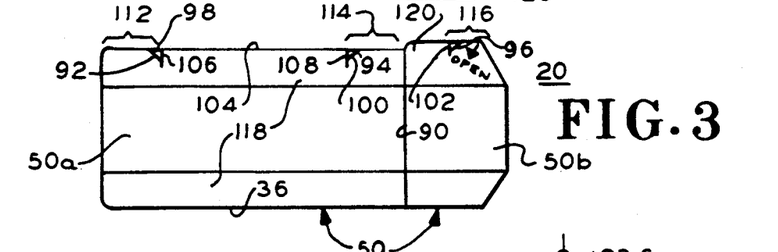
FIG. 3 is a plan view of the retainer of FIG. 1 completely folded.

Formed at the boundary 34 and into the panels 32 and 46 are V-shaped cuts 92, 94 and 96. The apices of the V's 92, 94, 96 are located on the boundary 34 with the legs thereof extending away from the boundary 34 on either side thereof. (FIG. 1). After the third panel 46 is folded, the legs of each V overlie each other to define a locking ear 98, 100 and 102 which is comprised of overlying segments of material of both panels 32 and 46. Formed in the free longitudinal boundary or edge 104 of the fourth panel 50 are perpendicular slits 106, 108 and 110. The slits 106, 108 and 110 define lock tabs 112, 114 and 116 in the portions 50a and 50b of the fourth panel 50 (FIG. 2). After the third panel 46 is folded and held by the tab-slit pairs 74/86 and 76/88, the panel 50 (that is, the fourth and fifth panels 50a and 50b thereof) is folded about the boundary 36 to overlie the previously folded and held third panel 46 (FIG. 3). In this position of the panel 50, portions of the lock tabs 112, 114 and 116 adjacent the slits 106, 108 and 110 are moved under their respective locking ears 98, 100 and 102 (FIG. 3) to close the retainer 20 and maintain the folded panel 50 as shown in FIG. 3.

The outside surface of the folded panel 50 may bear indicia, such as one or more colored areas 118 or other printed data which permit quick, accurate identification of the type of strand 24 in the suture 22. The surface of the panel 50 may also contain printed data or other indicia, including bar codes, conveying information regarding matters such as the type, number, size and length of the suture 22; the quantity and type of needles 26; an indication, if appropriate, that the retainer 20 is sterile; a reorder code or number for the retainer 20; the name and address of the manufacturer or supplier; and the lot number. In a preferred embodiment, the fifth panel 50b bears at least the suture identifying colored strips 118 and indicia regarding needle description and count and recorder number. The panel 50b is separable from the retainer 20 along the gusset 52 and may be attached to medical procedure documents for subsequent verification of needle count following use of the suture 22.

Figure 4:
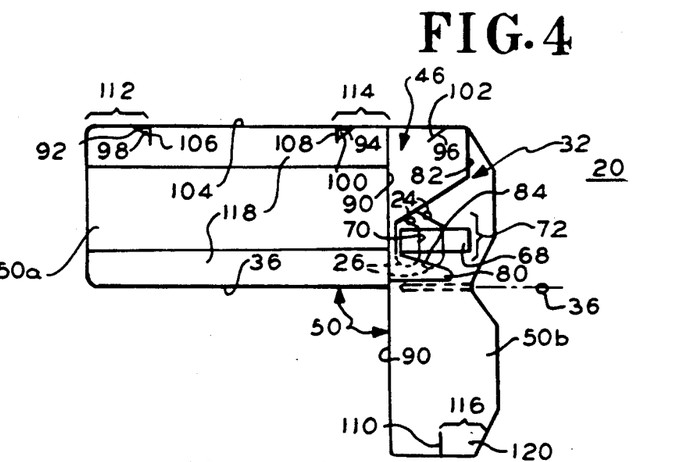
FIG. 4 is a plan view of the retainer of FIG. 3 a portion of which has been unfolded to provide access to a suture therein for the removal thereof.

As can be seen in FIGS. 1 and 4, the transverse dimension of the cover portion or fifth panel 50b is preferably slightly greater than that of the main portion or fourth panel 50a and of the first panel 32 as covered by the third panel 46. This results in the cover portion 50b having a digit-engageable lift tab 120, by which the cover portion 50b can be selectively unfolded about the boundary 36 to expose the sutures 22 at the withdrawal site 72 through the opening 84 as shown in FIG. 4.

As should be obvious, the terms "boundary," "edge" and "folding line" may refer to either or both a non-discontinuous boundary or folding line, such as that 34 between the panels 32 and 46, and a discontinuity or true edge, such as the free edges 38, 78 and 104. As already noted the edges between the various panels 32, 42, 46 and 50 are, in view of the integral nature of the planar member 30, not discontinuous and are "invisible" boundaries or fold lines, except insofar as the gussets 44, 48 and 52 or the slits 86 and 88 render them visible.

In describing the embodiments of FIGS. 5-12, the use of the reference numerals found in FIGS. 1-4 indicates elements which are the same as or similar to the corresponding elements shown in the latter FIGS.

Figures 5, 6:
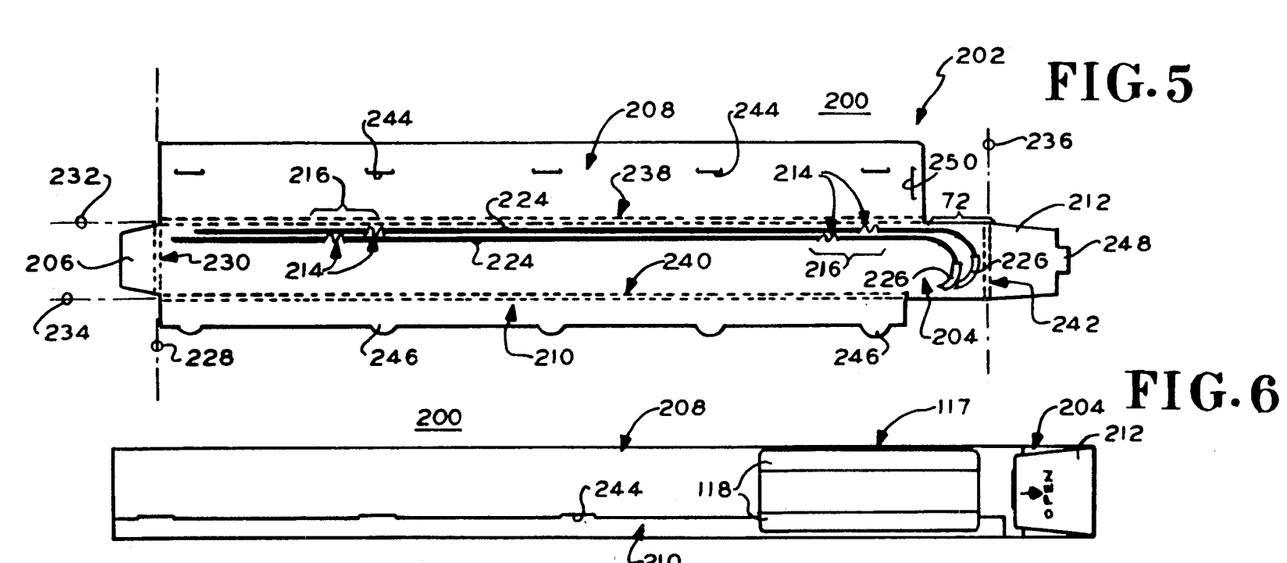
FIG. 5 is a plan view of the second embodiment of a suture retainer according to the present invention, the retainer being unfolded.
FIG. 6 is a plan view of the retainer of FIG. 5 completely folded.
Figures 5A, 7:
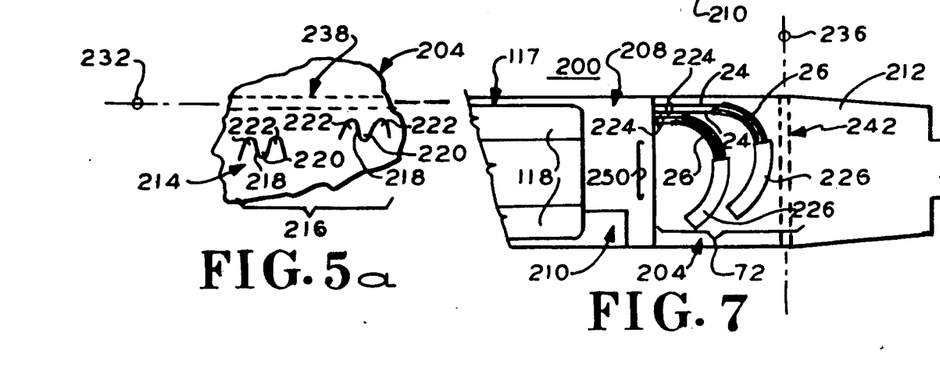
FIGS. 5a and 5b are enlarged view of portions of the retainer of FIG. 5 showing certain details thereof.
FIG. 7 is a partial plan view of the retainer of FIG. 6 with a portion unfolded to provide access to sutures therein for the removal thereof.

A second embodiment 200 of the retainer shown in FIGS. 5-7 is intended primarily for use with sutures 22 in which the suture strands 24 are relatively stiff stainless steel wires, although other sutures 22 having different suture strands 24 may be packaged therein.

Figure 5B:
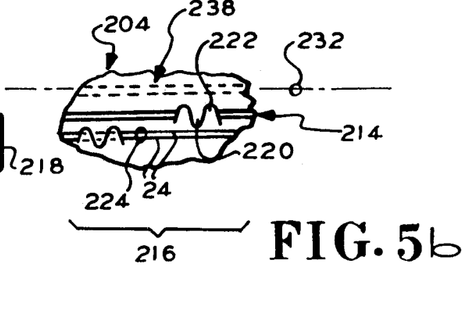

The retainer 200 is stamped or die cut from appropriate paper or card as a planar number 202 having first through fifth panels 204, 206, 208, 210 and 212. The first panel 204 is an elongated rectangle with four holding and separating features 214 located in pairs at two sites 216. The features 214 (see FIG. 5a) comprise W-shaped or M-shaped cuts 218 through the panel 204 each forming a central tab 220 located between adjacent side tabs 222. A suture strand 24 may be located beneath and held by one or more of the tabs 220 and 222 but is preferably intended to run along the surface of the panel 204 and to run under all of the tabs 220 and 222 of the features 214, as shown in FIG. 5b. The cuts 218 produce sufficient flexibility at the features 214 so that the strands 24 may be worked beneath the tabs 220 and 222 which may be selectively deformed outwardly as necessary for this purpose.

Each feature 214 is aligned with another feature 214 along the long axis of the panel 204 and the sites 216 are separated along the axis to hold and support the strands 24 near their respective ends. The features 214 of this embodiment 200 serve much the same function as the separator 56 of FIGS. 1-4, by preventing the strands 24 from becoming entangled and facilitating the withdrawal thereof from the retainer 200 while maintaining the separate strands 24 apart.

As shown in FIGS. 5-7, pairs 224 of sutures 22, each comprising a strand 24 and on attached needle 26, run along the panel 204 and are held by longitudinally aligned features 214 at each site 216. Alternatively, each suture pair 224 may be replaced by a single suture 22 having a single strand 24 with a needle 26 attached to each free end 28 thereof. As shown in FIG. 7, the needles 26 of each pair 224 may be held together in general alignment by a protective tube or sheath 226. The sheath 226, which may be fabricated of medical grade silicone rubber, covers and protects the needles 26 and their points while permitting the shanks of the needles 26 and their points of attachment to the free ends 28 of the strands 24 to be presented and accessible at a withdrawal site 72 on the surface of the panel 204. In use, the sheath 226 may be removed with a forceps or the like, followed by removal of one needle 26 and its trailing strand 24, which slides under and past the tabs 220 and 222 of the features 214. Alternatively, both sutures 22 of a given pair 224 may be removed together, with the sheath 226 remaining in place. Thereafter, the sheath 226 is removed and the sutures 22 put to use.

The second panel 206 is foldably connected to the panel 204 along a boundary, edge or folding line 228. The boundary 228 may include double perforated fold lines 230 or equivalent folding gussets, score lines or the like. Similarly the third, fourth and fifth panels 208, 210 and 212 are foldably connected to the panel 204 along respective boundaries, edges or folding lines 232, 234 and 236, which may include double perforated fold lines 238, 240 and 242 or their functional equivalents. Each panel 206-212 is generally rectangle and is generally coextensive with its associated boundary 228 and 232-236 of the panel 204, except that the long dimensions of the panels 208 and 210 are shorter than that of the panel 204, with the panel 208 being slightly longer than the panel 210.

After the sutures 22 are emplaced on the panel 204, the second panel 206 is folded to prevent the strands 24 from moving beyond the boundary of the panel 204. Thereafter the panel 208 is folded to overlie the sutures 22 and the panel 210 is next folded thereover. Slits 244 in the panel 208 and inserted tabs 246 on the free edge of the panel 210 hold the panel 210 folded. The panel 212 is then folded and a tab 248 thereon is inserted into a slit 250 formed in the panel 208 to maintain the retainer 200 closed. The panel 212 covers the withdrawal site 72 and the needles 26 and strands 24 therein. As shown in FIG. 6, the retainer 200 may be held positively closed by adhering a label 117 to the panel 210 and to the exposed portion of the panel 208. The label 117 and/or the surface of the panel 208 may carry the colored areas 118 and various data and indicia, as described above regarding FIGS. 1-4. Removing the tab 248 from the slit 250 permits the panel 212 to be unfolded to expose the withdrawal site for withdrawal of the sutures 22.

A third retainer embodiment 300 shown in FIGS. 8-12 is similar to the embodiment 200 but includes some features of the embodiment 20. The third embodiment 300 is intended for use with sutures 22 having a single suture strand 24 and a needle 26 at either end thereof, although other sutures 22 may obviously be used.

Figure 8:
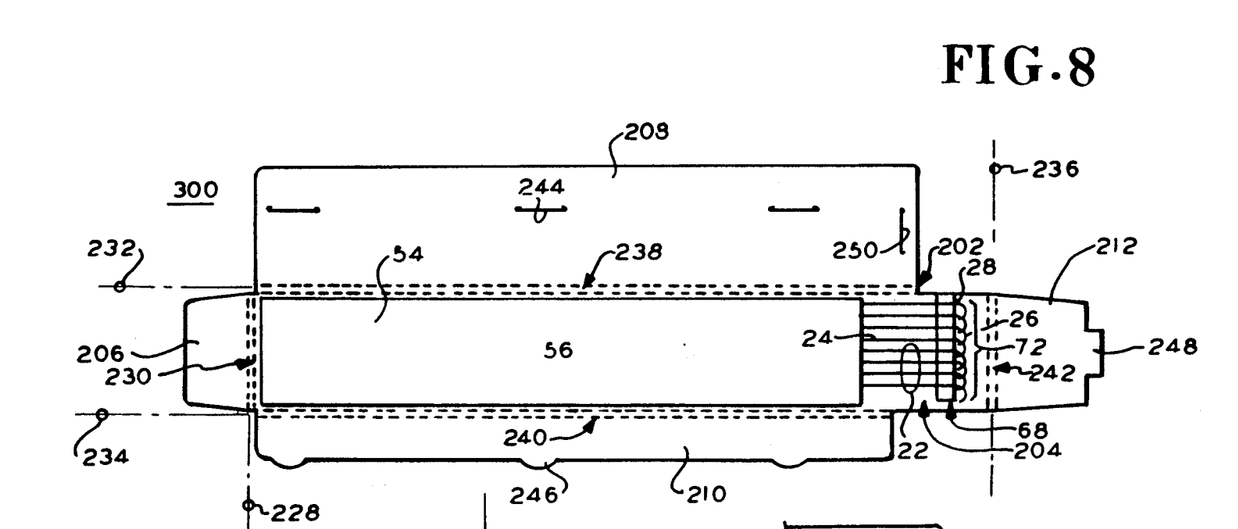
FIG. 8 is a plan view of a first version of a third embodiment of a suture retainer according to the present invention, the retainer being unfolded.
Figure 9:
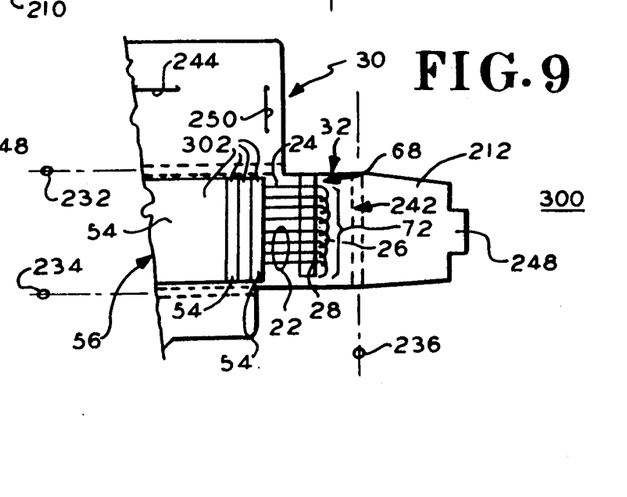
FIG. 9 is a partial plan view of a second version of the third embodiment shown in FIG. 8.
Figure 10:
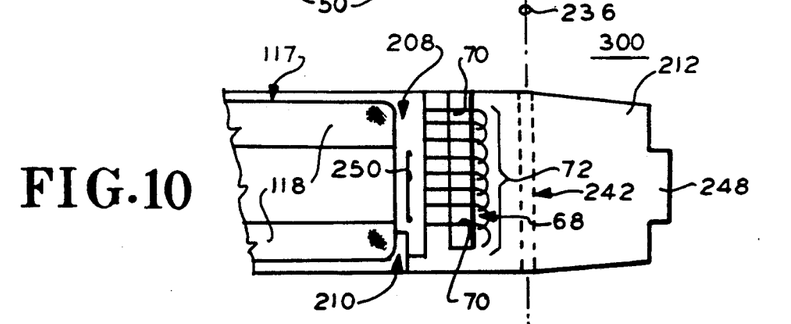
FIG. 10 is a partial plan view of the first version of the third embodiment shown in FIG. 8, the retainer being folded with a portion unfolded to provide access to sutures therein for selective removal thereof.
Figure 11:
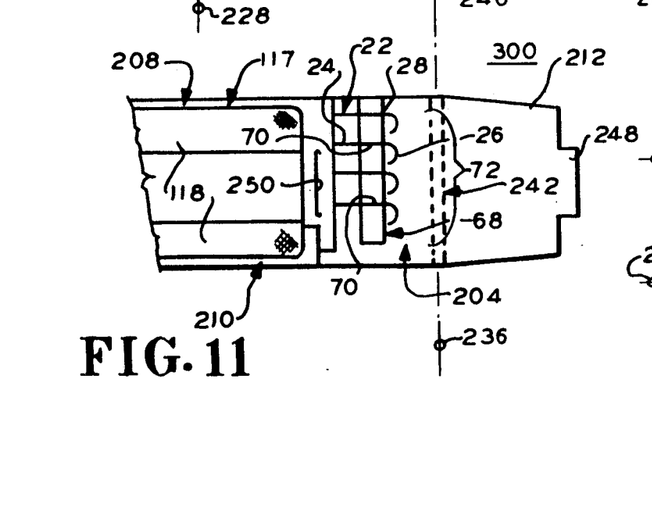
FIG. 11 is a partial plan view of a third version of the third embodiment of FIG. 8 the retainer being folded similarly with a portion unfolded to provide access to sutures therein for selective removal thereof.
Figure 12:
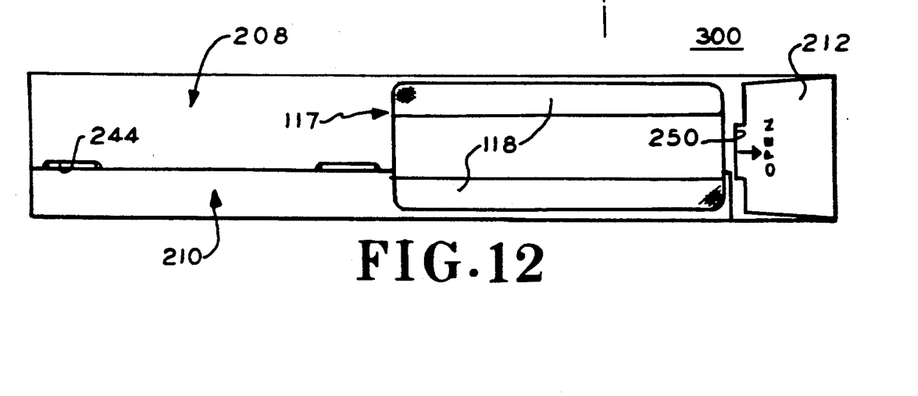
FIG. 12 is a plan view of the retainers of FIGS. 8-11 in a fully folded condition.

The embodiment 300 includes the planar member 202, the five panels 204-212, the boundaries 228 and 232-236, the fold lines 230 and 238-242, and the slit tab combinations 244/246 and 250/248, all similar to those shown in FIGS. 5-7. Each version of the third embodiment 300 includes the foam strip 68 with the slits 70 therein similar to that of FIGS. 1-4, except that, the strip 68 is aligned with and closely parallel to the boundary 236 and the fold lines 242 between the panels 204 and 212 rather than the boundary 234 as in FIG. 1. The slits 70 frictionally hold the sutures 22. In FIGS. 8, 9 and 10, each free end 28 of the strands 24 and its associated needle 26 is individually maintained at the withdrawal site 72 in a single slit 70, with the needles 26 associated with a given strand 24 being immediately adjacent. In FIG. 11, the related needles 26 of each suture 22 are together maintained at the removal site 72 by a single slit 70 which frictionally holds both ends of the associated strand 24.

In FIG. 8, the separator 56 is present. The separator 56 is accordion-folded and the strands 24 of each two-needle suture 22 are held between respective pairs of adjacent leaves 54 of the separator. In FIG. 9, the separator 56 comprises a plurality of two-leaved envelopes 302, each holding both runs of the single strand 24 of each suture 22. The separators 56 of either type prevent tangling of the strands and facilitate the withdrawal thereof. The separator 56 of FIG. 8 is adhered to the panel 204 as in FIG. 1. The bottom envelope 302 of the stack of envelopes 302 comprising the separator 56 of FIG. 9 is similarly adhered to the panel 204, with superjacent envelopes 302 being similarly adhered thereto and to each other.

Figure 13:
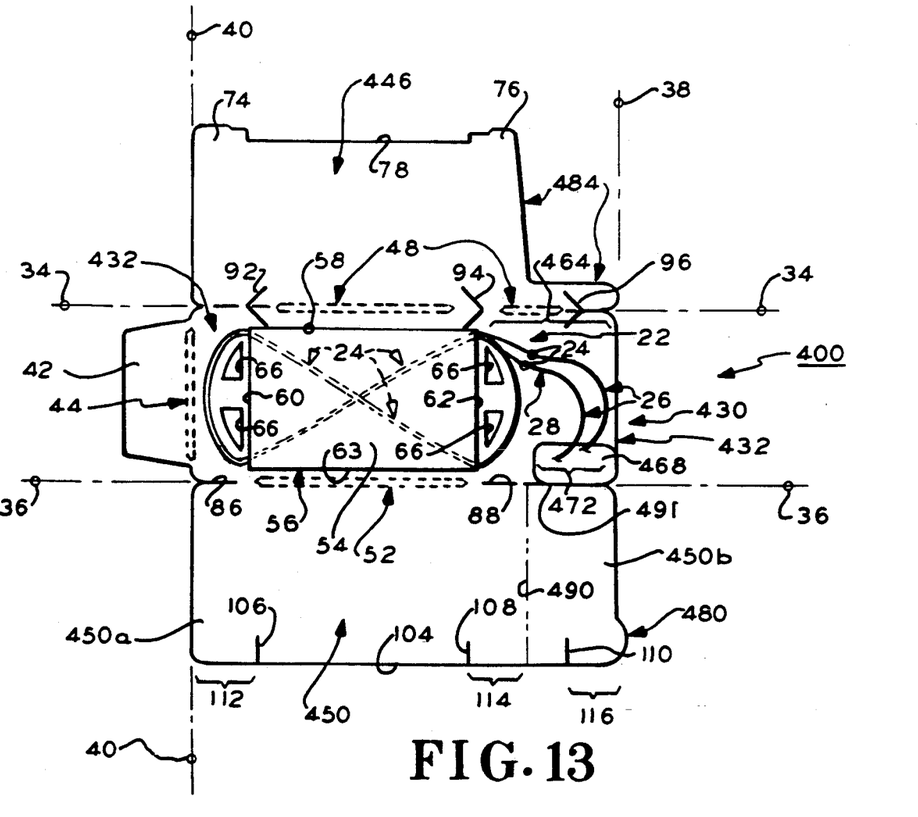
FIG. 13 is a plan view similar to FIG. 1 of a fourth embodiment of a retainer according to the present invention, the retainer being unfolded.
Figure 14:
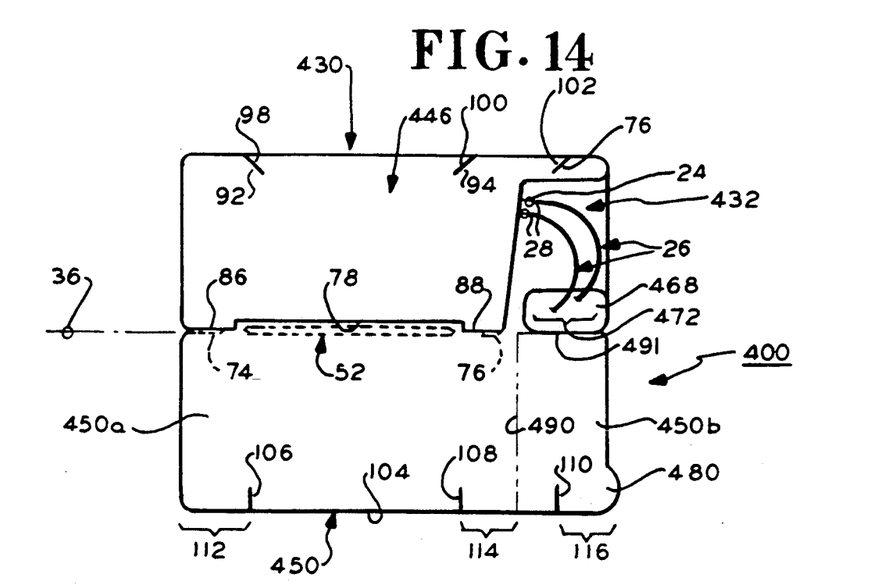
FIG. 14 is a plan view of the retainer of FIG. 13 partially folded.
Figure 15:
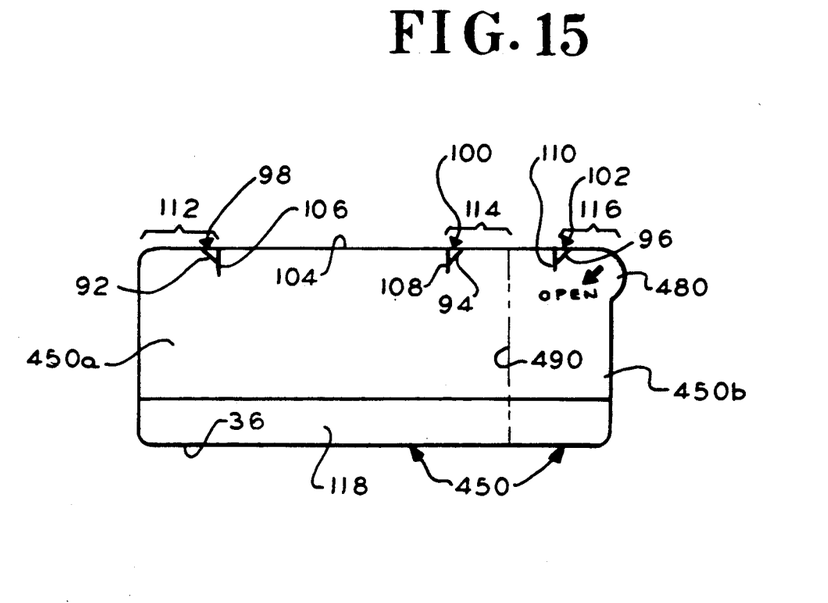
FIG. 15 is a plan view of the retainer of FIG. 13 completely folded.
Figure 16:
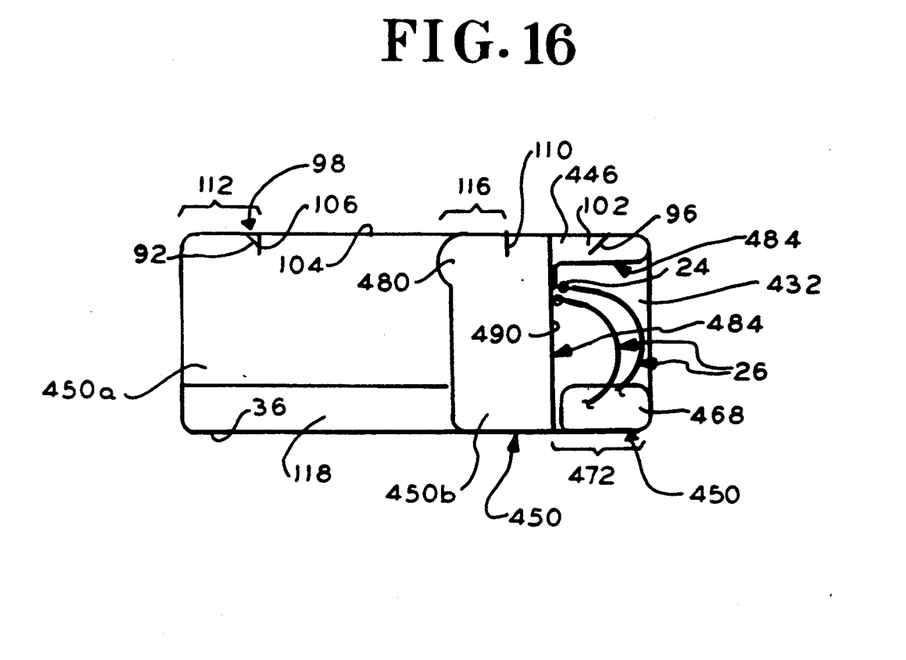
FIG. 16 is a plan view of the retainer of FIG. 15, a portion of which has been unfolded to provide access to a suture therein for the removal thereof.

Referring now to FIG. 13, there is shown a fourth embodiment 400 of a suture retainer for retaining one or more sutures 22, each of which comprises a suture strand 24 and one or more surgical needles 26. The embodiment of FIG. 13 and related FIGS. 14-16 is a variation of that shown in FIGS. 104, similar elements are identified with the same or similar reference numerals.

The needles 26 are attached to free ends 28 of the suture strand 24 in any convenient fashion. In FIGS. 13-16, the suture 22 comprises a single suture strand 24 with a needle 26 attached to each free end 28 thereof. The retainer 400 of could also, of course, be used with a plurality of sutures 22 each comprising a suture strand 24 and a single needle 26 attached to one free end 28.

The retainer 400 is stamped or die cut as a generally irregular planar member 430 from an appropriate robust paper or card such as medical grade S.B.S. bleached white or other suitable material.

The planar member 430 is initially flat and includes a first generally rectangular panel 432 defined by opposed, parallel longitudinal boundaries, edges or fold lines 34 and 36 and opposed, parallel transverse boundaries, edges or fold lines 38 and 40 which are normal to the boundaries 34 and 36. A second generally rectangular panel or flap 42 is integral with the panel 432 along the boundary or fold line 40. The second panel 42 is foldable relative to the first panel 432 via a folding gusset 44 or a similar facility such as score lines, double perforated fold lines, or the like, present along the boundary 40.

A third generally rectangular panel 446 is integral with panel 432 along the boundary 34. The third panel 446 is foldable relative to the first panel 432 via one or more folding gussets 48 or similar facilities present along the boundary 34. A generally rectangular panel 450 is also integral with the panel 432 along the boundary 36 and is similarly foldable via one or more folding gussets 52 or the like present along the boundary 36. The panels 446 and 450 are generally rectangularly complementary to the panel 432 except as noted hereinafter. The second panel 42 is substantially shorter along its shorter dimension than the long dimension of the panel 432.

The suture strand 24 is preferably wound in a figure-8 pattern and is held between the low friction leaves 54 of a separator 56, only a top leaf 54 of which is visible in FIG. 13. As viewed in FIG. 13, the separator 56 has two leaves 54 folded along a hinge line 58. The separator may comprise a sheet of suitable robust, low-friction material, such as sterilizable (e.g., ETO and/or Gama) blue or natural glassine, folded along the hinge line 58 to form a rectangular separator 56 may be mounted to the first panel 432. The separator 56 may be mounted to the first panel 432 by the use of a suitable adhesive, such as an FDA-approved cyano-acrylateester adhesive. The separator 56 is mounted to the surface of the panel 432 so that its left lateral edge 60 is closer to the boundary 40 than the spacing of its right lateral edge 62 from the boundary 38. The fold line 58 and the opposed longitudinal edges 63 of the leaves 54 are substantially respectively equidistantly spaced from the boundaries 34 and 36. The foregoing relative positioning of the panel 432 and the separator 56 creates an open region 464 on the surface of the panel 432 for the purposes described below.

To aid in winding the suture strand 24, the first panel 432 may include a plurality of apertures 66 through which winding posts (not shown) may selectively protrude. With the posts protruding through the apertures 66, the strand 24 is wound thereabout in a figure-8 while the upper leaf 54 of the separator 56 is held open along the hinge line 58 to lie against the third panel 446. After the strand 24 has been wound in the figure-8 or other selected pattern, the posts are withdrawn and the upper leaf 54 is folded thereover. The low friction nature of the separator 56 facilitates easy tangle-free withdrawal of the strand 24 and, hence, easy release of the suture 22 in use. Where multiple sutures 22 and multiple suture strands 24 are held in the retainer 400, the separator 56 may comprise an accordion-folded sheet with on figure -8 wound strand 24 of each suture 22 between adjacent leaves 54. In this event, the separator 56 prevents the suture strands 24 from becoming entangled with each other. In all cases, the separator 56 prevents the strand 24 from taking an undesirable set, a problem which is acute with strand 24 such as monofilament polypropylene.

A strip 468 is mounted within the open region 464 to the first panel 432 by a suitable adhesive (not shown), such as an FDA-approved pressure-sensitive adhesive. The strip 468 is preferably a medical grade plastic foam onto which the adhesive is previously coated. The strip 468 is located between the boundary 38 and the edge 62 and is proximate to and parallel with the boundary 36. Before the strand 24 is wound, the points of the needles 26 are "parked" or penetrated into the surface of the foam strip 468 to mechanically engage and hold the needles 26 stationary. To this end, the density or grade of the strip 468 may be varied to vary the mechanical engagement force, while preventing damage to the point of the needles 26. This engagement holds the needles 26 stationary during winding of the strand 24 and maintains the needles 26 spaced apart and stabilized at a suture withdrawal site 472 within the region 464. The withdrawal site 472 is located quite near to the boundary 36 of the first panel 432 and between the edge 62 and the boundary 38.

After the needles 26 of the suture 22 are held by the strip 468 and the strand 24 is wound, the second panel 42 is folded along the boundary 40 to overlie the edge 60 of the separator 56 and any of the loop-like portion of the Figure -8 wound strand 24 which may protrude past such edge 60. The folded panel 42 insures that the wound strand 24 is retained within the perimeter of the first panel 432 and does not extend beyond the boundary 40 where it could snag or be damaged.

The third panel 446 includes closing tabs 74 and 76 formed on the free longitudinal boundary or edge 78 thereof. The third panel is also believed to include a needle access opening 484. The needle access opening 484 may be conveniently produced by removal of some of the material of the panel 446 along the boundaries or edges 38 and 78. The opening 484 is dimensioned and located so that when the third panel 446 is folded along the boundary 34 to overlie the second panel 42 and the separator 56 (FIG. 14), the shanks of the needles 26 and the free ends 28 of the strands 24 at the withdrawal site 472 are exposed through the opening 484. The points of the needles 26 remain covered and protected by the foam strip 468 while permitting the sutures 22 to be selectively withdrawn. Withdrawal of the suture 22 is achievable by grasping a selected needle 26 with forceps near the free end 28 of its strand 24, lifting and rotating the needle 26 to free the point of needle 26 from the foam strip 468 and moving the now freed suture 22 rightwardly (in FIGS. 14 or 16) until the needle 26 clears the opening 484. The suture 22 is then withdrawn by pulling the strand 24 out of the separator 56 while uncoiling the figure -8. If the needles 26 are attached to opposite free ends 28 of the single strand 24, continued unwinding of the figure -8 will ultimately require withdrawal of the point of the second needle 26 from the foam strip 468.

The boundary 36 contains slits 86 and 88 into which the tabs 74 and 76 may be respectively inserted after the third panel 446 has been folded to overlie the first panel 432. see FIG. 14. This locks and maintains the folded panel 446 in its folded position.

The panel 450 comprises a main portion 450a and a cover portion 450b. The portions 450a and 450b are integral, but the portion 450b is easily foldable relative to the portion 450a along a perforation or score line 490. The portion 450b is separable from the panel 432 at boundary 36 by a slit 491 which runs along boundary 36 form boundary 38 to boundary 490. The main portion 450a itself may be viewed as the fourth panel, while the cover portion 450b may be viewed as a fifth panel.

Formed at the boundary 34 and into the panels 432 and 446 are V-shaped cuts 92, 94 and 96. The apices of the V's 92, 94 and 96 are located on the boundary 34 with the legs thereof extending away from the boundary 34 on either side thereof (FIG. 13). After the third panel 446 is folded, the legs of each V overlie each other to define locking ears 98, 100 and 102 which comprise overlying segments of material of both panels 432 and 446. Formed in the free longitudinal boundary or edge 104 of the fourth panel 450 are perpendicular slits 106, 108 and 110. The slits 106, 108 and 110 define lock tabs 112, 114 and 116 in the portions 450a and 450b of the fourth panel 450. After the third panel 446 is folded and held by the tab/slit pairs 74/86 and 76/88, the panel 450 (that is, the fourth and fifth panels 450a and 450b thereof) is folded about the boundary 36 to overlie the previously folded and held third panel 446 (FIG. 15). In this position of the panel 450, portions of the lock tabs 112, 114 and 116 adjacent the slits 106, 108 and 110 are moved under their respective locking ears 98, 100, 112 (FIG. 15) to close the retainer 400 and maintain the folded panel 450 as shown in FIG. 15.

The outside surface of the folded panel 450 may bear indicia, such as one or more colored areas 118 or other printed data which permit quick, accurate identification of the type of strand 24 included in the suture 22. The surface of the panel 450 may also contain printed data or other indicia, including bar codes, conveying information regarding matters such as the type, number, size and length of suture 22; the quantity and type of needles 26; an indication, if appropriate, that the retainer 400 is sterile; a reorder code or number for the retainer 400; the name and address of the manufacturer or supplier; and the lot number. In a preferred form of this embodiment, the fifth panel 450b bears at least the suture identifying colored strip 118 and indicia regarding needle description and count and reorder number. The panel 450b is separable from the retainer 420 along perforation or score line 490 and may be attached to medical procedure documents for subsequent verification of needle count following use of the suture 22.

As can be seen in FIGS. 13 and 16, the cover portion 450b includes a digit-engageable lift tab 480, by which the cover portion 450b can be selectively lifted and folded about fold line 490 onto cover portion 450a to expose the sutures 22 at the withdrawal site 472 through the opening 484 as shown in FIG. 16.

The above describes exemplars of the present invention which are covered hereafter by the appended claims. Numerous changes of and additions to these exemplars may be made without departing from the spirit and scope hereof.

We claim:

1. A retainer for a suture, the retainer comprising:
   (a) a first generally rectangular panel;
   (b) a multi-leaved, generally rectangular separator for holding between adjacent folds thereof a wound suture strand, the separator being adhered to the first panel so that an end of the held suture strand with a needle attached thereto is extendable to reside between first adjacent transverse edges of the separator and the first panel;
   (c) a second generally rectangular panel foldably connected to the second transverse edge of the first panel for selective folding about the edge to overlie both the second transverse edge of the separator and any portion of the held suture strand extending therebeyond;
   (d) a third generally rectangular panel foldably connected to one longitudinal boundary of the first panel for selective folding about the boundary to complementarily overlie the first panel and to overlie and cover the folded second panel and the separator;
   (e) means for holding the strand end generally normal to the other longitudinal boundary of the first panel so that the attached needle is maintained at a withdrawal site;
   (f) a tab on the third panel which, with the third panel folded, overlies the point of the needle at the withdrawal site but exposes the attachment of the needle to the suture strand;
   (g) a fourth generally rectangular panel foldably connected to the other longitudinal boundary of the first panel for selective folding about the boundary to complementarily overlie the folded third panel and the withdrawal site;
   (h) means located on both (i) the boundary between the first and third panels and (ii) the free longitudinal edge of the fourth panel, for maintaining the folded fourth panel in its folded, overlying position; and
   (j) a cover portion of the fourth panel, which cover portion is unfoldable independently of the remainder of the fourth panel and about the boundary between the first and fourth panels to expose the withdrawal site and the strand-needle attachment and to permit withdrawal of the strand from the holding means and of the needle from beneath the tab and the concomitant withdrawal of the strand from the separator within the folded panels.

2. A retainer as in claim 1 for a multiply needled suture, wherein:
the wound suture is held between adjacent leaves of the separator, and
the free suture ends are held side-by-side by the holding means at the withdrawal site.

3. A retainer as in claim 2, wherein:
the separator is a low friction material.

4. A retainer as in claim 1 for multiple sutures, wherein:
the separator is accordion-folded and each suture is held between respective adjacent leaves thereof.

5. A retainer as in claim 4, wherein:
the separator is a low friction material.

6. A retainer as in claim 1, wherein:
the first panel includes apertures through which winding posts are protrudable for winding the suture thereabout, following which the posts are withdrawn.

7. A retainer as in claim 6, wherein:
the suture is wound in a figure-8 pattern overlying one leaf of the separator.

8. A retainer as in claim 1, wherein:
the holding means comprises:
a strip adhered to the first panel at the withdrawal site, the strip having a slit in which the suture strand is frictionally held.

9. A retainer as in claim 8, wherein:
the strip extends along the other longitudinal boundary of the first panel.

10. A retainer as in claim 9, wherein:
the strip is a foamed plastic.

11. A retainer as in claim 8, wherein:
the slit is normal to the other longitudinal boundary of the first panel.

12. A retainer as in claim 8, wherein:
with the third panel folded, the tab on the third panel and the strip are generally parallel.

13. A retainer as in claim 1, wherein:
the maintaining means comprises:
a V-shaped cut in the first and third panels having its apex lying on the one longitudinal boundary of the first panel, the two legs of the V overlying each other when the third panel is folded to thereby define a locking ear, and
a slit formed in the -free longitudinal edge of the fourth panel to define a locking tab along such edge, a portion of the locking tab being insertable under the locking ear after the fourth panel is folded.

14. A retainer as in claim 1, which further comprises:
means for retaining the third panel in its folded condition before the fourth panel is folded.

15. A retainer as in claim 14, wherein:
the retaining means comprises
a lock tab on the free edge of the third panel, and a slit formed along the boundary between the first and fourth panels, the lock tab being insertable into the slit after the third panel is folded.

16. A retainer as in claim 1, which further comprises: suture-identifying indicia on the cover portion.

17. A retainer as in claim 16, wherein: the cover portion is separable from the first panel.

18. A retainer for a suture having a suture strand and a needle attached to an end thereof, the retainer comprising
(a) a first generally rectangular panel;
(b) a multi-leaved, generally rectangular separator for holding between adjacent folds thereof the suture strand, the separator being adhered to the first panel so that the end of the held suture strand with the needle attached thereto is extendable to reside between first adjacent transverse edges of the separator and the first panel;
(c) a second generally rectangular panel foldably connected to the second traverse edge of the first panel for selective folding about the edge to overlie the second transverse edge of the separator;
(d) a third generally rectangular panel foldably connected to one longitudinal boundary of the first panel for selective folding about the boundary to complementarily overlie the first panel and to overlie and cover the folded second panel and the separator;
(e) means for holding the strand end proximate to a boundary of the first panel so that the attached needle is maintained at a withdrawal site;
(f) a fourth generally rectangular panel foldably connected to the other longitudinal boundary of the first panel for selective folding about the boundary to overlie a substantial portion of the folded third panel;
(g) a fifth generally rectangular panel foldably connected to a boundary of the first panel for selective folding about the boundary to overlie the withdrawal site;
(h) first selectively releasable means located at least in part on both (i) the third panel and (ii) the free longitudinal edge of the fourth panel, for maintaining the folded fourth panel in its folded condition; and
(j) second selectively releasable means located at least in part on both (i) the third panel and (ii) a free edge of the fifth panel, for maintaining the folded fifth panel in its folded condition, so that the fifth panel is unfoldable independently of the fourth panel to expose the withdrawal site and the strand-needle attachment and to permit withdrawal of the strand from the holding means and of the needle from the withdrawal site and the concomitant withdrawal of the strand from the separator within the folded panels.

19. A retainer as in claim 18, wherein: the fourth and fifth panels are foldably connected to the same boundary of the first panel, with the fifth panel being unfoldable independently of the folded fourth panel.

20. A retainer as in claim 19, which further comprises: a tab on the third panel which, with the third panel folded, overlies the point of the needle at the withdrawal site but exposes the needle-strand attachment.

21. A retainer as in claim 19, wherein:

the first and second selectively releasable means are located on both (i) the boundary between the first and third panels and (ii) the free longitudinal edges of the fourth and fifth panels.

22. A retainer as in claim 18, wherein: the fifth panel a foldably connected to the first transverse edge of the first panel.

23. A retainer as in claim 22 for use with multiple sutures, wherein:
the separator is accordion-folded, one suture strand of each suture residing between each adjacent pair of leaves.

24. A retainer as in claim 22 for use with multiple sutures, wherein:
the separator comprises a stack of two-leaved envelopes, one suture strand of each suture residing within one of the envelopes.

25. A retainer as in claim 22, wherein:
the holding means is a strip of flexible material adhered to the first panel at the withdrawal site, the strip having a slit in which the suture strand is frictionally held.

26. A retainer as in claim 25 for use with a suture having a needle attached to each end thereof, wherein:
the strip contains side-by-side slits for respectively frictionally holding the ends of the suture strand and its associated needles side-by-side.

27. A retainer as in claim 25 for use with a suture having a needle attached to each end thereof, wherein:
both ends of the suture strand are frictionally held in the slit to maintain their associated needles in superjacency.

28. A retainer as in claim 27 for use with multiple sutures, wherein:
the strip contains side-by-side slits for respectively frictionally holding both ends of each suture strand and its associated needles in superjacency with the needle pairs being side-by-side.

29. A retainer as in claim 19, which further comprises: suture-identifying indicia on the fifth panel.

30. A retainer as in claim 29, wherein: the fifth panel is separable from the first panel.

31. A retainer for a suture having a suture strand and a needle attached to an end thereof, the retainer comprising:
(a) a first generally rectangular panel;
(b) separator means on the first panel proximate the first transverse edge thereof for preventing tangling of the suture strand, for facilitating free movement of the suture strand along the first panel, and for normally maintaining the suture strand stationary relative to the first panel;
(c) a second generally rectangular panel foldably connected to the second transverse edge of the first panel for selective folding about the edge to prevent movement of the suture strand beyond the boundary of the first panel;
(d) a third generally rectangular panel foldably connected to one longitudinal boundary of the first panel for selective folding about the boundary to complementarily overlie the first panel and to overlie and cover the folded second panel and the separator means;
(e) means for holding the end of the suture strand with the needle attached hereto proximate to a boundary of the first panel so that the needle is maintained at a withdrawal site;

(f) a fourth generally rectangular panel foldably connected to the other longitudinal boundary of the first panel for selective folding about the boundary to overlie a substantial portion of the folded third panel;

(g) a fifth generally rectangular panel foldably connected to a boundary of the first panel for selective folding about the boundary to overlie the withdrawal site;

(h) first selectively releaseable means located at least in part on both (i) the third panel and (ii) the free longitudinal edge of the fourth panel, for maintaining the folded fourth panel in its folded condition; and (j) second selectively releaseable means located at least in part on both (i) the third panel; and (ii) a free edge of the fifth panel, for maintaining the folded fifth panel in its folded condition, so that the fifth panel is unfoldable independently of the fourth panel to expose the withdrawal site and the strand-needle attachment and to permit withdrawal of the suture strand from the holding means and the needle from the withdrawal site and the concomitant withdrawal of the strand from the separator means within the folded panels.

32. A retainer as in claim 31, wherein:

the separator means comprises a W-shaped or M-shaped cut formed through the first panel to define a central tab and two side tabs adjacent thereto, the suture strand being extendable along the first panel and under the tabs for frictional holding thereof.

33. A retainer as in claim 32, wherein:

the first panel contains a plurality of longitudinally spaced tab-defining cuts, the tabs of which frictionally hold the extended strand at a plurality of spaced locations.

34. A retainer as in claim 33 for use with multiple sutures, wherein:

a series of the longitudinally spaced cuts transversely spaced apart each frictionally hold one of the strands at spaced locations so that the strands are kept separated and extend along the first panel generally parallel to each other 35. A retainer as in claim 31 which further comprises:

means for covering the point of the needle while exposing the strand-needle attachment, the covering means being separate from and underlying the folded fifth panel.

36. A retainer as in claim 35, wherein:

the covering means is a sheath surrounding a portion of the needle and overlying its point.

37. A retainer as in claim 35, wherein:

the covering means is a tab on the third panel which, with the third panel folded, overlies the point of the needle.

38. A retainer as in claim 31, wherein:

the fourth panel when folded partially overlies the third panel, and which further comprises:

a label adhered to the folded fourth panel and the exposed portion of the third panel.

39. A retainer as in claim 38, which further comprises:

suture-identifying indicia on the label.

40. A retainer for a suture having a suture strand and a needle attached to an end thereof, the retainer comprising:

(a) a first generally rectangular panel;

(b) separator means on the first panel proximate the first transverse edge thereof for preventing tangling of the suture strand and for facilitating free movement of the suture strand along the first panel;

(c) a second generally rectangular panel foldably connected to the second transverse edge of the first panel for selective folding about the edge;

(d) a third generally rectangular panel foldably connected to one longitudinal boundary of the first panel for selective folding about the boundary to complementarily overlie the first panel and to overlie and cover the folded second panel and the separator means;

(e) means for holding the strand end and the needle attached thereto proximate to a boundary of the first panel so that the attached needle is maintained at a withdrawal site;

(f) a fourth generally rectangular panel foldably connected to the other longitudinal boundary of the first panel for selective folding about the boundary to overlie a substantial portion of the folded third panel;

(g) a fifth generally rectangular panel foldably connected to the retainer so as to be foldable independently of the fourth panel to selectively overlie or expose the withdrawal site;

(h) first selectively releaseable means located at least in part on both (i) the third panel and (ii) the free longitudinal edge of the fourth panel, for maintaining the folded fourth panel in its folded condition; and (j) second selectively releaseable means located at least in part on both (i) the third panel; and (ii) a free edge of the fifth panel, for maintaining the folded fifth panel in its folded condition, so that the fifth panel is unfoldable independently of the fourth panel to expose the withdrawal site and the strand-needle attachment and to permit withdrawal and the needle from the withdrawal site and the concomitant withdrawal of the strand from the separator means within the folded panels.

41. A retainer as in claim 37, wherein:

the fifth panel is foldably connected to the other longitudinal boundary of the first panel.

42. A retainer as in claim 37, wherein:

the fifth panel is foldably connected to a transverse edge of the fourth panel, which edge is spaced from, and extends in generally the same direction as, the first transverse edge of the first panel.

43. A retainer as in claim 37, wherein:

the holding means comprises a strip adhered to the first panel at the withdrawal site, the point of the needle being insertable into, and being frictionally held by, the strip.

44. A retainer as in claim 40, wherein:

the strip extends along the other longitudinal boundary of the first panel.

45. A retainer as in claim 41, wherein:

the strip is a foamed plastic.

46. A retainer as in claim 42, wherein:

the fifth panel is foldably connected to a transverse edge of the fourth panel, which edge is spaced from, and extends in generally the same direction as, the first transverse edge of the first panel.

* * * * *

UNITED STATES PATENT AND TRADEMARK OFFICE
CERTIFICATE OF CORRECTION

PATENT NO. : 5,101,968
DATED : April 7, 1992
INVENTOR(S) : Scott Henderson and James A. Wimbush It is certified that error appears in the above-indentified patent and that said Letters Patent is hereby corrected as shown below:

Column 16, first line of Claim 41, change "37" to -- 40 --. Column 16, first line of Claim 42, cancel "37" and insert -- 40 --. Column 16, first line of Claim 43, cancel "37" and insert -- 40 --. Column 16, first line of Claim 44, cancel "40" and insert -- 43 --. Column 16, first line of Claim 45, cancel "41" and insert -- 44 --. Column 16, first line of Claim 46, cancel "42" and insert -- 45 --.

Signed and Sealed this

Eighth Day of June, 1993

Attest:

MICHAEL K. KIRK

*Attesting Officer*  Acting Commissioner of Patents and Trademarks